United States Patent
Boedeker

Patent Number: 5,924,612
Date of Patent: Jul. 20, 1999

[54] INFANT TRANSPORT DEVICE

[76] Inventor: Douglas W. Boedeker, 4911 Branen Dr., Washington Courthouse, Ohio 43160

[21] Appl. No.: 08/862,766

[22] Filed: May 23, 1997

Related U.S. Application Data

[60] Provisional application No. 60/018,231, May 24, 1996.

[51] Int. Cl.$^6$ .................................................. A61G 1/00
[52] U.S. Cl. .......................... 224/158; 294/140; 604/356
[58] Field of Search .................................... 604/356, 357; 224/158, 159; 128/845; 294/140, 149, 152

[56] References Cited

U.S. PATENT DOCUMENTS

| | | | |
|---|---|---|---|
| 39,766 | 9/1863 | Wheeler | 224/158 |
| 719,206 | 1/1903 | Faulkner | 604/357 |
| 1,741,838 | 12/1929 | Gilbert | 604/357 |
| 3,034,132 | 5/1962 | Landsberger et al. | 2/69.5 |
| 4,616,365 | 10/1986 | Lyons | 2/69 |
| 4,817,836 | 4/1989 | Bates | 604/356 |
| 4,944,057 | 7/1990 | Shaw | 294/152 |
| 4,963,138 | 10/1990 | Braun | 604/357 |
| 4,979,250 | 12/1990 | Troncone et al. | 5/494 |
| 5,046,204 | 9/1991 | Mohler | 5/413 |
| 5,321,863 | 6/1994 | Yamaguchi et al. | 5/655 |
| 5,432,965 | 7/1995 | Espinoza | 5/482 |
| 5,449,004 | 9/1995 | Sanchez | 224/158 |

*Primary Examiner*—Mark O. Polutta
*Attorney, Agent, or Firm*—Biebel & French

[57] ABSTRACT

An infant transport device is formed of a generally rectangular section of soft and absorbent blanket or towel material having laterally spaced apart and integrally formed sleeves extending along opposed side marginal edges. Sleeves are open adjacent a front or proximal edge of the material and are closed at the forward or distal edge of the material with a closure which forms a mitten to receive a hand. The device has a width which is sufficient to receive an infant between the arms of an attendant which has been inserted within the two sleeves formed on the device and has a length from front to back which exceeds the height of the infant so that the entire body of the infant may be placed between the arms on the device and cradled or held in a sling-like manner. Thumb openings are formed adjacent the closed ends by which an attendant can extend the thumbs through the mitten portion for securing an infant or to aid and assist in gripping.

3 Claims, 2 Drawing Sheets

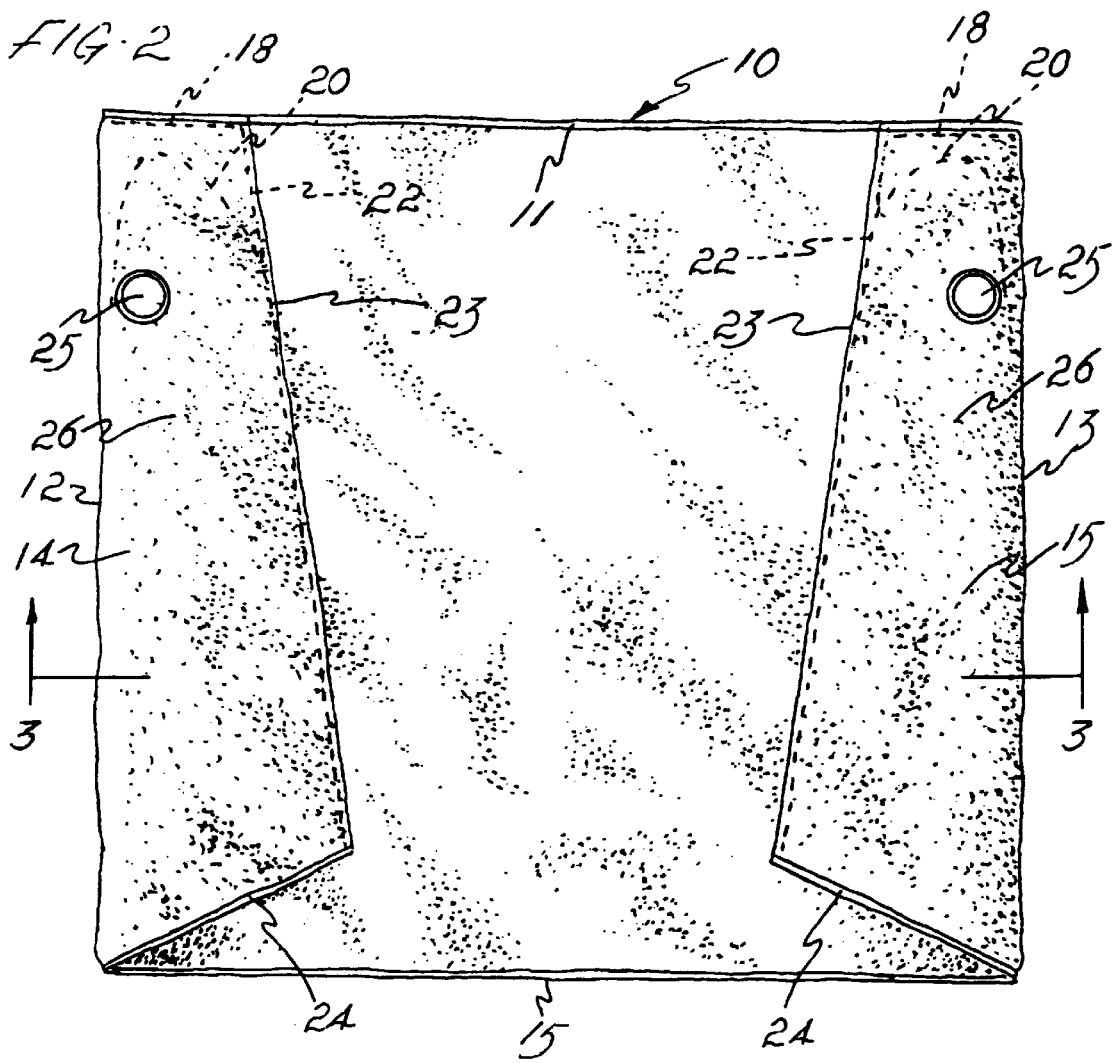
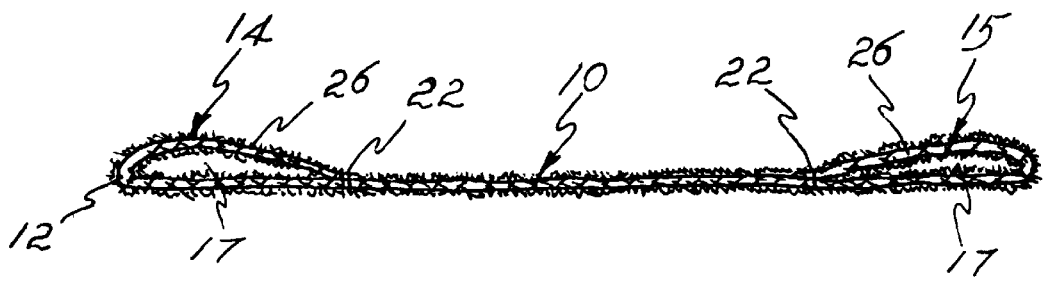

INFANT TRANSPORT DEVICE

CROSS-REFERENCE TO RELATED APPLICATION

Benefit of the co-pending U.S. Provisional Application entitled "Infant Transport Device," Ser. No. 60/018,231 filed May 24, 1996, Attorney Docket BOO 001 P2-USP is claimed.

BACKGROUND OF THE INVENTION

This invention relates to an infant transport device and more particularly to a low cost, safe, and sure device by which a newborn infant may be handed from the hands of the delivering doctor or other person to the hands of a nurse for transport to a nearby warming table for warming, stimulating, and drying the infant, and providing increased assurance that the infant will be cradled and safely transported.

The post-natal care apparatus and facilities have undergone rapid and remarkable improvement for the health and safety of both the mother and the newborn child. However, there is one aspect of the birthing process, as normally practiced in birthing rooms and in operating rooms which is open to some risk of mishandling and an opportunity for serious injury to the infant, and that could occur during the infant's first post-natal trip in which the infant is placed in the waiting towel or blanket held by an assistant and is carried to a warming table. Usually, if not always, in a hospital environment, the infant is handed to an assistant who is carrying a blanket or towel and who holds the infant and the blanket or towel together, turns, and carries the infant to the warming table area for drying and stimulating. This action, on the part of the assistant, must be accomplished with great care, as such person uses gloved hands to grip the newborn and the towel together, so that this task may be safely accomplished. Thus, if a corner of the towel or blanket is dropped or becomes unfolded, the infant may be placed in jeopardy or subjected to a risk of mishandling or even falling. That such accidents are extremely rare testifies to the skill and care of attendants, and not to any adequate transport device specifically designed, constructed, and intended for this purpose.

The presentation of the newborn child from the mother to an attendant is essentially the same whether the child is born naturally or whether the child is taken by c-section. The latter is normally accomplished within a sterile field and therefore any object which is brought into the room and used for this purpose usually should also be sterile lest the field of sterilization be broken.

Conventional blankets, towels, or other swaddling clothes are not adapted for support of the infant, as such, unless they are formed and gripped properly by the attendant. There is accordingly a need for an infant transport device which assures a higher degree of safety which is uncomplicated and easy to use, which permits an attendant freely to use his or her hands also in supporting the infant, which is absorbent, and which upon arrival at the warming table, may be used immediately for drying and stimulating the infant according to conventional practices.

SUMMARY OF THE INVENTION

The invention is directed to an infant transport device, in the form of a generally rectangular section of soft and absorbent blanket or towel material which is formed with a pair of laterally spaced apart and integrally formed sleeves extending along opposed marginal edges. The sleeves are open adjacent one edge of the device, namely the edge that is closest to the body of the user. The sleeves are closed at the opposite forward edge, with a smooth curvature in the nature of a mitten.

The body of the device has width or spacing laterally of the side edges sufficient to receive an infant between the arms of an attendant which have been inserted one within each of the two sleeves, and has the length from front to back is in excess of the height of such an infant so that the entire body of the infant may be placed, in sling-like manner, on the material suspended between the supporting arms when the arms are held forward from the body.

Each of the integral arm sleeves is formed, adjacent the closure or mitten end, with an upwardly opening thumb hole through which a gloved thumb of the attendant is inserted. In this manner, the attendant whose arms are free to be manipulated within the mitten, has a thumb extending through each of the thumb holes which may be used in a gripping manner to engage a leg or arm of the infant and to secure the transport device. These sleeve sections may be formed integrally with the body of the support device by overlying a section of fabric and is sewn or secured along the margins thereof, leaving sleeve entrance openings at the side closest to the attendant.

When the infant is so placed, the attendant, merely by raising the arms, brings the baby closer to the attendant's body where the baby is snuggled and securely cradled. When the attendant arrives at the warming table, since the attendant's arms are already in the transport device, the attendant may now use these encased arms and enclosed fingers to fold the absorbent material of the transport device over the child and proceed to begin to wipe and stimulate the infant's body. Thereafter, the attendant may easily withdraw the arms because the weight of the infant will hold the transportation device in place, leaving the infant resting on the transport device which, in appropriate circumstances, may become an item of bedding or blanket, or may be disposed of.

It is contemplated that the device may be formed of disposable absorbent and soft material such as cotton, cotton terry cloth, or cotton and polyester blends of blanket-like materials, which are suitable for absorbing moisture and rubbing the baby, and which have more than sufficient wet tensile strength to hold the newborn baby sling-like, suspended between the arms. Also, the transport device may be formed of completely sterile material so that its use and entry into the sterile field will not break or compromise the sterility of the field.

It is accordingly an important object of this invention to provide an infant transport device which enhances the safety of supporting and transporting a newborn infant from the hands of the delivering person such as to a remote warming table or the like.

A further object of the invention is the provision of a combined blanket or towel-like member particularly adapted to be worn on a pair of arms with a portion of the hands extended into pockets or mitten portions and with a thumb exposed through a thumb hole providing a positive gripping of the device and permitting normal manipulation of the hands, and providing a transport cradle for safely transporting a newborn infant.

These and other objects and advantages of the invention will be apparent from the following description, the accompanying drawings and the appended claims.

BRIEF DESCRIPTION OF THE DRAWINGS

FIG. 2 is a plan view of the infant transport device; and

FIG. 3 is a sectional view taken generally along the line 3,3 of FIG. 2.

DESCRIPTION OF PREFERRED EMBODIMENT

Figure 1:
FIG. 1 is a perspective view of the infant transport device of this invention in use.

Referring first to FIG. 2, which shows a plan view of the transport device looking at the exposed upper surface, it will be seen that the invention comprises substantially a body 10 of sheet-like material in a rectangular shape with an outer edge 12, a pair of parallel side edges 13 and 14, and an inner edge 15. The body is preferably made of a lightweight and strong absorbent yet soft material, such as soft cotton terry cloth, toweling material or cotton or cotton blend pile type blanket material. The material must have sufficient tensile strength to support the weight of the baby, in a wet condition, and should be absorbent to absorb fluids and to be useful in assisting in the drying of the infant. A suitable non-woven fiber product may be used such as now used for non-woven diapers and the like, provided it has sufficient wet strength to support the weight of the infant.

The body 10 includes a pair of spaced apart arm-receiving integral sleeves 14 and 15 formed respectively along side edges 12 and 13. The sleeves 14 and 15 are formed of a folded-over portion of the material. They each form an arm-receiving opening 17 at a position adjacent the inner edge 15 (FIG. 2). The sleeves are closed by stitching 18 adjacent the forward or outer edge 12. Further, the forward portion of each of the sleeves 14 and 15 is closed with a second curved line of stitching 20 generally in the shape of a mitten to define the extent to which an arm and hand may be inserted into the sleeve through the opening 17. The sleeve is further defined by stitching 22 which joins the respective inner edges 23 of the sleeves to the body 11. The sleeves 14 and 15, therefore, are open along the margin or inner edge 15, and for ease of entry, the entrance edge 24 of the sleeves may be tapered to expose a portion of the body, as shown.

Each of the sleeves is provided with a reinforced thumb opening 25 defined as a hole cut into the flap 26 which forms the upper surface of the sleeve to permit the exit of a gloved thumb therethrough. The thumb opening 25 is reinforced and in the case of cloth material, it may be whip stitched such as in the case of a button hole, or zigzag stitched, to provide suitable reinforcement. The holes 25 are proportioned to permit the thumb to be extended therethrough when the fingers are comfortably in the mitten portion defined by the curved line of stitching 20. The sleeves 14 and 15 are proportioned comfortably to be received on the forearms and up to or slightly beyond the elbows of an attendant, as shown in FIG. 1. In this condition, the major portion of the infant's body extends between these supporting arms and is somewhat depressed as a sling or hammock, while the hands may be used to elevate or raise the forward or outer edge 12 to provide a safe and soft pocket for an infant, such as represented by the infant 30 in FIG. 1.

In use, an attendant will be standing by, with the device 10 on the arms, will receive the infant from the delivering person and immediately move it to a position where it may be treated for any particular problem, such as a breathing problem, or particularly moved to a warming table where the infant may be stimulated and dried conventionally and safely. The device 10 cannot slip off the arms by reason of the superior gripping ability of the forearms and thumb, nor can the infant slip off the hammock-like cradle defined in the body 10 between the arms since the infant may be cuddled and brought up close to the bosom of the attendant during transfer.

After birth, the device 10 may continue to be useful as a towel for the mother's bassinet, such as for handling and drying a bathed infant. Further, the device 10 may be useful in the kits of emergency ambulances to be used by trained paramedics for emergency handling of infants, newborns, or injured small persons, such as burn victims, as the cases may arise.

By way of example, without limitation, a device has been made which is 24 inches across at the forward edge 11 and across the rear or inner edge 15. The side edges 12 and 13 are each 25 inches long, and the sleeves 14 and 15 are eight inches wide at the entrance opening 17 and five inches wide across the seam 18. The thumb holes are approximately one and one-quarter inches in diameter and spaced 20 inches apart, center-to-center.

While the form of the apparatus herein described constitutes a preferred emobidment of this invention, it is to be understood that the invention is not limited to this precise form of apparatus, and that changes may be made therein without departing from the scope of the invention which is defined in the appended claims:

What is claimed is:

1. A transport device for handling and carrying an infant, such as a newborn infant, comprising a sheet-like body of soft absorbent material having a forward edge, a pair of side edges, and a back edge, an integral portion of said body being folded over and sewn to said body defining thereby a pair of laterally spaced sleeves defined by a fold along the side edges, said folded over material being attached to said body to form integral enclosed sleeves which are open at said back edge, said sleeves being closed at said forward edge, each of said sleeves being provided with an opening proportioned to receive the thumb of a person whose arms are inserted within such sleeves, with a major portion of the body of said device extending between the arms and forming a sling for supporting an infant between said sleeves.

2. An infant handling and transport device comprising a generally rectangular body of flexible and absorbent sheet-like material having therein a pair of laterally spaced integral sleeves defining lateral edges of said body and being open at one end thereby and proportioned to permit the arms of a person one each to be extended into such sleeves, each of such sleeves being closed at a forward end thereof to form mitten-like sleeve ends for receiving the fingers of a wearer and each of such sleeves being formed with an opening therethrough permitting a thumb to be extended out of such sleeves, with the body of said device between said sleeves being of sufficient transverse width and length along said sleeves to receive an infant thereon.

3. An infant transport device comprising a generally rectangular section of soft and absorbent blanket or towel material having a pair of laterally spaced apart and integrally formed sleeves extending along lateral marginal edges thereof with closed forward end and an intermediate portion integrally extending between said sleeves and having proportions such as to receive an infant thereon between said sleeves, each of said sleeves being proportioned to permit the arms of an attendant to be inserted therein one in each of said sleeves, the length of said section being in excess of the height of an infant so that the entire body of an infant may be placed between said sleeves in a sling-like manner and suspended between supporting arms inserted in said sleeves, and thumb openings formed in each of said sleeves adjacent said forward ends thereof permitting a thumb of a hand to be extended therethrough when arms are inserted in said sleeves.

* * * * *